United States Patent
Bryant et al.

(10) Patent No.: US 6,407,243 B1
(45) Date of Patent: Jun. 18, 2002

(54) BENZOFURAN COMPOUNDS, COMPOSITIONS, AND METHODS

(75) Inventors: Henry U. Bryant, Indianapolis; George J. Cullinan, Trafalgar; Jeffrey A. Dodge, Indianapolis; Kennan J. Fahey, Indianapolis; Charles D. Jones, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/435,437

(22) Filed: May 10, 1995

Related U.S. Application Data

(62) Division of application No. 08/309,271, filed on Sep. 20, 1994.

(51) Int. Cl.[7] .................. C07D 405/10; A61K 31/445
(52) U.S. Cl. .................. 546/196; 540/596; 544/153; 548/525; 549/462; 514/212; 514/255; 514/320; 514/422; 514/443
(58) Field of Search .................. 514/212, 255, 514/320, 422, 443; 540/596; 544/153; 546/196; 548/525; 549/462

(56) References Cited

U.S. PATENT DOCUMENTS

| | | | |
|---|---|---|---|
| 3,274,213 A | 9/1966 | Lednicer | 260/326.5 |
| 3,293,263 A | 12/1966 | Lednicer | 260/326.5 |
| 3,313,853 A | 4/1967 | Lednicer | 260/570.7 |
| 3,320,271 A | 5/1967 | Lednicer | 260/307 |
| 3,394,125 A | 7/1968 | Crenshaw | 260/326.5 |
| 3,396,169 A | 8/1968 | Lednicer | 260/294.7 |
| 3,413,305 A | 11/1968 | Crenshaw | 260/326.5 |
| 3,483,293 A | 12/1969 | Duncan et al. | 424/274 |
| 3,567,737 A | 3/1971 | Lednicer | 260/326.5 |
| 3,862,232 A | 1/1975 | Lednicer | 260/570.7 |
| 3,947,470 A * | 3/1976 | Brenner | 549/467 |
| 3,983,245 A * | 9/1976 | Ladd | 549/467 |
| 4,133,814 A | 1/1979 | Jones et al. | 260/326.5 |
| 4,230,862 A | 10/1980 | Suarez et al. | 546/237 |
| 4,380,635 A | 4/1983 | Peters | 546/202 |
| 4,418,068 A | 11/1983 | Jones | 424/267 |
| 4,851,554 A * | 7/1989 | Kennedy | 549/471 |
| 5,254,568 A | 10/1993 | Kapil et al. | 514/320 |
| 5,523,309 A * | 6/1996 | Bryant | 514/320 |
| 5,622,974 A * | 4/1997 | Muehl | 514/320 |

FOREIGN PATENT DOCUMENTS

| | | |
|---|---|---|
| EP | 0 124 369 | 11/1984 |
| JP | WO93/10113 | 5/1993 |
| WO | WO93/1074 | 6/1993 |
| WO | 95/10513 * | 4/1995 |

OTHER PUBLICATIONS

Jones et al. "Antiestrogens. 2. Structure–activity studies . . . " J. Med. Chem. p. 1057, 1984.*
Erber et al. "2–phenylbenzo[b]furans:relationship between structure, estrogen receptor affinity and cytostatic activity against mammary tumor cells" CA 116:120397 (1991).*
Crenshaw, R.R., et al., *J. Med. Chem.*, 14(12):1185–1190 (1971).
Durani, N., et al., *Indian J. Chem.*, 22B:489–490 (1983).
Jones, C.D., et al., *J. Med. Chem.*, 35:931–938 (1992).
Cerny, et al., *Tetrahedran Letters*, 8:691–694 (1972).
Lednicer, D., et al., *J. Med. Chem.*, 8:52–57 (1964).
Lednicer, D., et al., *J. Med. Chem.*, 9:172–175 (1965).
Lednicer, D., et al., *J. Med. Chem.*, 10:78–84 (1967).

* cited by examiner

*Primary Examiner*—Ceila Chang
(74) *Attorney, Agent, or Firm*—Gary M. Birch; Gilbert T. Voy; Steven A. Fontana

(57) ABSTRACT

The present invention provides novel compound of the formula:

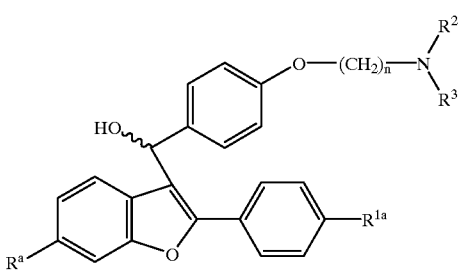

wherein
$R^a$ is —OH or
—O—($C_1$–$C_4$ alkyl);
$R^{1a}$ is —OH or
—O—($C_1$–$C_4$ alkyl);
n is 2 or 3;
$R^2$ and $R^3$ are each independently:
—$C_1$–$C_4$ alkyl, or
combine to form
1-piperidinyl,
1-pyrrolidinyl,
1-pyrrolidinyl substituted with one or two methyl groups,
4-morpholino or
1-hexamethyleneimino;
or a pharmaceutically acceptable salt thereof.

15 Claims, No Drawings

BENZOFURAN COMPOUNDS, COMPOSITIONS, AND METHODS

This application is a division of pending prior application Ser. No. 08/309,271, filed on Sep. 20, 1994.

FIELD OF THE INVENTION

This invention relates to the fields of pharmaceutical and organic chemistry and provides novel benzofuran compounds which are useful for the treatment of the various medical indications associated with post-menopausal syndrome, and uterine fibroid disease, endometriosis, and aortal smooth muscle cell proliferation. The present invention further relates to intermediate compounds useful for preparing the pharmaceutically active compounds of the present invention, and pharmaceutical compositions. Furthermore, the present invention relates to a novel process for preparing the pharmaceutically active compounds of the present invention.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, colles fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, Tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new benzofuran compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Smooth aortal muscle cell proliferation plays an important role in diseases such as atherosclerosis and restenosis.

Vascular restenosis after percutaneous transluminal coronary angioplasty (PTCA) has been shown to be a tissue response characterized by an early and late phase. The early phase occurring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal*, 122: 171–187 (July 1991).

In the pathogenesis of restenosis excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

SUMMARY OF THE INVENTION

The present invention relates to compounds of formula I

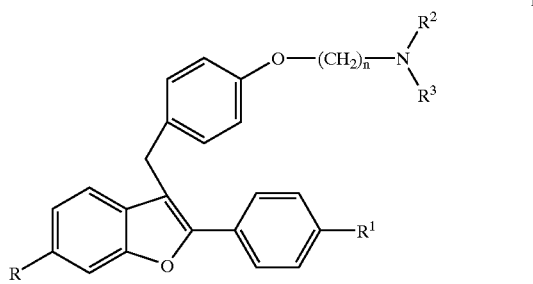

wherein
R is —H, —OH, —O($C_1$-$C_4$ alkyl), —O—CO—($C_1$-$C_6$ alkyl), —O—CO—Ar in which Ar is optionally substituted phenyl, or —O—$SO_2$—($C_4$-$C_6$ alkyl);
$R^1$ is —H, —OH, —O($C_1$-$C_4$ alkyl), —O—CO—($C_1$-$C_6$ alkyl), —O—CO—Ar in which Ar is optionally substituted phenyl, —O—$SO_2$—($C_4$-$C_6$ alkyl), chloro or bromo;

n is 2 or 3; and

R² and R³ each are independently C₁–C₄ alkyl, or combine to form 1-piperidinyl, 1-pyrrolidinyl, methyl-1-piperidinyl, dimethyl-1-piperidinyl, 4-morpholino, or 1-hexamethyleneimino;

or a pharmaceutically acceptable salt thereof.

Also provided are compounds of formula IX which are useful for preparing compounds of formula I.

The present invention also relates to pharmaceutical compositions containing compounds of formula I, optionally containing estrogen or progestin, and the use of such compounds, alone, or in combination with estrogen or progestin, for alleviating the symptoms of post-menopausal symptoms, particularly osteoporosis, cardiovascular related pathological conditions, and estrogen-dependent cancer. As used herein, the term "progestin" includes compounds having progestational activity such as, for example, progesterone, norethynodrel, norgestrel, megestrol acetate, norethindrone, and the like.

The present invention further relates to the use of the compounds of the present invention for inhibiting uterine fibroid disease and endometriosis in women and aortal smooth muscle cell proliferation, particularly restenosis, in humans.

Furthermore, the present invention relates to a process for preparing a compound of formula Ia

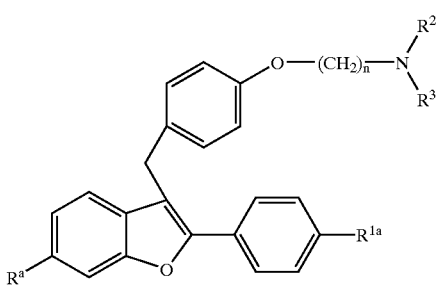

wherein $R^a$ and $R^{1a}$ each are —OH or —O(C₁–C₄ alkyl);

R² and R³ each are independently C₁–C₄ alkyl, or combine to form C₄–C₆ polymethylene, —CH₂CH(CH₃)CH₂CH₂—, —CH₂C(CH₃)₂CH₂CH₂—, or —CH₂CH₂OCH₂CH₂—; and n is 2 or 3; or a pharmaceutically acceptable salt thereof, which comprises a) optionally dealkylating a compound of formula II

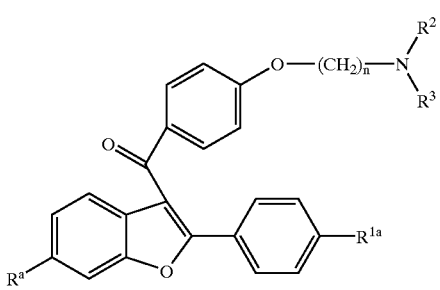

wherein $R^a$, $R^{1a}$, R², R³, and n are as defined above;

b) reacting said formula II compound with a reducing agent in the presence of a solvent having a boiling point in the range from about 150° C. to about 200° C., and heating the mixture to reflux; and c) optionally salifying the reaction product form step b).

DETAILED DESCRIPTION OF THE INVENTION

One aspect of the present invention includes compounds of formula I

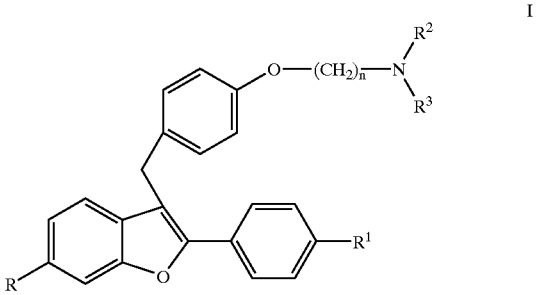

wherein

R is —H, —OH, —O(C₁–C₄ alkyl), —O—CO—(C₁–C₆ alkyl), —O—CO—Ar in which Ar is optionally substituted phenyl, or —O—SO₂—(C₄–C₆ alkyl);

R¹ is —H, —OH, —O(C₁–C₄ alkyl), —O—CO—(C₁–C₆ alkyl), —O—CO—Ar in which Ar is optionally substituted phenyl, —O—SO₂—(C₄–C₆ alkyl), chloro or bromo;

n is 2 or 3; and

R² and R³ each are independently C₁–C₄ alkyl, or combine to form 1-piperidinyl, 1-pyrrolidinyl, methyl-1-piperidinyl, dimethyl-1-pyrrolidinyl, 4-morpholino, or 1-hexamethyleneimino; or a pharmaceutically acceptable salt thereof.

General terms used in the description of compounds herein described bear their usual meanings. For example, "C₁–C₄ alkyl" refers to straight or branched aliphatic chains of 1 to 4 carbon atoms including methyl, ethyl, propyl, isopropyl, butyl, n-butyl, and the like; and "C₁–C₆ alkyl" encompasses the groups included in the definition of "C₁–C₄ alkyl" in addition to groups such as pentyl, isopentyl, hexyl, isohexyl, and the like.

The term "substituted phenyl" refers to a phenyl group having one or more substituents selected from the group consisting of C₁–C₄ alkyl, C₁–C₅ alkoxy, hydroxy, nitro, chloro, fluoro, or tri(chloro or fluoro)methyl. "C₁–C₅ alkoxy" represents a C₁–C₅ alkyl group attached through an oxygen bridge such as, for example, methoxy, ethoxy, n-propoxy, isopropoxy, and the like.

The compounds of the present invention are derivatives of benzo [b] furan which is named and numbered according to the Ring Index, The American Chemical Society, as follows

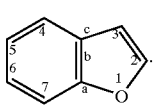

The starting materials of the present invention, compounds of formula II below, are made essentially as described in U.S. Pat. No. 4,133,814, issued Jan. 9, 1979, U.S. Pat. No. 4,418,068, issued Nov. 29, 1983, and U.S. Pat. No. 4,380,635, issued Apr. 19, 1983, each of which is herein incorporated by reference. This process provides a convenient process which acylates a methylated starting compound and then optionally dealkylates it to obtain the desired dihydroxy product. The acylation and dealkylation may be performed in successive steps in a single reaction mixture or the intermediate may be isolated and the dealkylation step be performed in a separate reaction.

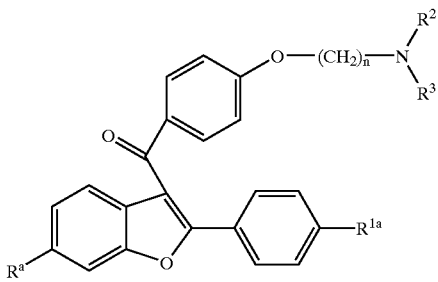

II wherein $R^a$, $R^{1a}$, $R^2$, $R^3$, and n are as defined above, or a salt thereof.

In the preparation of a formula II compound, an alkyl-protected compound of formula III

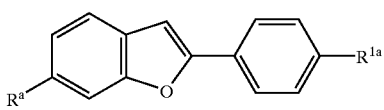

III is most easily obtained by reacting a 3-($C_1$–$C_4$ alkyl)phenol, preferably 3-methoxyphenol, and a-bromo-4-($C_1$–$C_4$ alkyl) acetophenone, preferably 4-methoxyacetophenone, in the presence of a strong base at a relatively low temperature, to form a-(3-methoxyphenoxy)-4-methoxyacetophenone, which is then ring closed with an agent such as polyphosphoric acid at a high temperature to obtain the intermediate compound of formula III.

The acylation of this invention is a Friedel-Crafts acylation, and is carried out in the usual way, using a Lewis acid such as aluminum chloride or bromide, preferably the chloride, as the acylation catalyst.

The acylation is ordinarily carried out in a solvent, and any inert organic solvent which is not significantly attacked by the conditions may be used. For example, halogenated solvents such as dichloromethane, 1,2-dichloroethane, chloroform, and the like may be used, as can aromatics such as benzene, chlorobenzene, and the like. It is preferred to use a halogenated solvent, especially dichloromethane.

It has been found that toluene is rather easily acylated under the conditions used in the Friedel-Crafts acylation. Therefore, it is important, when toluene is used in an earlier step of the process, to remove it as completely as possible from the protected starting compound. Furthermore, if toluene remains following preparation of a compound of formula IV below, it should be removed to avoid wasting the acylating agent and contaminating the product.

The acylations may be carried out at temperatures from about –30° C. to about 100° C., preferably at about ambient temperature, in the range of from about 15° C. to about 30° C.

The acylating agent is an active form of the appropriate benzoic acid of formula IV

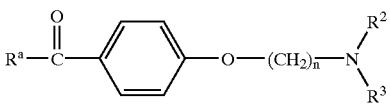

IV wherein $R^a$ is chloro or bromo, and $R^2$ and $R^3$ are as defined above. The preferred acylating agents are those wherein $R^a$ is chloro. Thus, using this reaction scheme, the most highly preferred individual acylating agents are 4-[2-(piperidin-1-yl)ethoxy]benzoyl chloride, 4-[2-(hexamethyleneimin-1-yl) ethoxy]benzoyl chloride, and 4-[2-(pyrrolidin-1-yl)ethoxy] benzoyl chloride.

The acyl chloride used as an acylating agent may be prepared from the corresponding carboxylic acid by reaction with a typical chlorinating agent such as thionyl chloride. Care must be taken to remove any excess chlorinating agent from the acyl chloride. Most conveniently, the acyl chloride is formed in situ, and the excess chlorinating agent is removed under vacuum.

It is generally preferred that an equimolar amount of the compounds of formulae III and IV are reacted together. If desired, a small excess of either reactant may be added to assure the other is fully consumed. It is generally preferred to use a large excess of the acylation catalyst, such as about 2–12 moles per mole of product, preferably about 5–10 moles of catalyst per mole of product.

The acylation is rapid. Economically brief reaction times, such as from about 15 minutes to a few hours provide high yields of the acylated intermediate. Longer reaction times may be used if desired, but are not usually advantageous. As usual, the use of lower reaction temperatures call for relatively longer reaction times.

The acylation step is ended and the optional dealkylation step is begun by the addition of a sulfur compound selected from the group consisting of methionine and compounds of the formula

wherein X is hydrogen or unbranched $C_1$–$C_4$ alkyl, and Y is $C_1$–$C_4$ alkyl or phenyl. The sulfur compounds are, preferably, the alkylthiols, such as methanethiol, ethanethiol, isopropanethiol, butanethiol, and the like; dialkyl sulfides, such as diethyl sulfide, ethyl propyl sulfide, butyl isopropyl sulfide, dimethyl sulfide, methyl ethyl sulfide, and the like; benzenethiol; methionine; and alkyl phenyl sulfides, such as methyl phenyl sulfide, ethyl phenyl sulfide, butyl phenyl sulfide, and the like.

It has been found that dealkylation is most efficient when a substantial excess of the sulfur compound is used, in the range of about 4 to about 10 moles per mole of the starting benzofuran. The process may be carried out, although less efficiently, with a smaller amount of the sulfur compound (in the range of about 2 to 3 moles per mole of the starting compound). It is also possible to use a small amount of the sulfur compound, and to improve the yield by the addition of about 1 to 3 moles of an alkali metal halide, such as sodium, potassium, or lithium chloride, bromide, or iodide.

The dealkylation reaction goes well at about ambient temperature, in the range of from about 15° C. to about 30° C., and such operation is preferred. The dealkylation may be carried out, however, at temperatures in the range of from about –30° C to about 50° C. if it is desired to do so. Short reaction times, in the range of about one hour, have been found to be sufficient.

After the product has been dealkylated, it is recovered and isolated by conventional means. It is customary to add water to decompose the complex of the acylation catalyst. Addition of dilute aqueous acid is often advantageous. The product precipitates in many instances, or may be extracted with an organic solvent according to conventional methods. The examples below further illustrate the isolation.

In an alternative, preferred process, an intermediate compound of formula V

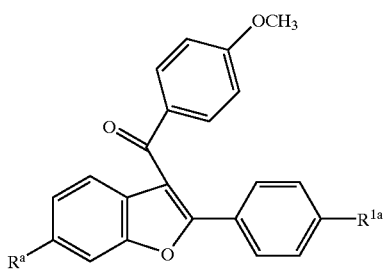

wherein $R^a$ and $R^1$ are as defined above, is prepared by the reaction of 2-hydroxy-4-methoxybenzaldehyde and 1-(4-($C_1$–$C_4$ alkoxy)phenyl)-2-(4-($C_1$–$C_4$ alkoxy)phenyl)ethanone, essentially as described in Preparation 3, infra. This reaction usually employs equimolar amounts of the two reactants although other ratios are operable. The reaction is performed in a non-reactive solvent such as ethyl acetate, chloroform, and the like, in the presence of an acid. Hydrochloric acid, particularly in the form of anhydrous hydrogen chloride, is an especially preferred acid. Lower alkyl alcohols are usually added to the non-polar solvent so as to retain more of the hydrochloric acid created in situ, with ethanol and methanol being especially preferred. The reaction is performed at temperatures ranging from ambient temperature up to the reflux temperature of the mixture. This reaction results in the preparation of the compound of formula VI

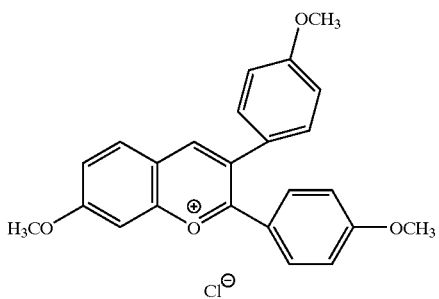

(or an equivalent anion if hydrochloric acid is not used), which is then oxidized to the compound of formula V by the action of hydrogen peroxide. The intermediate of formula VI may be isolated or may preferably be converted to the compound of Formula V in the same reaction vessel.

The compound of formula V is then selectively dealkylated, essentially as described in Preparation 4, infra, to yield the compound of formula VII

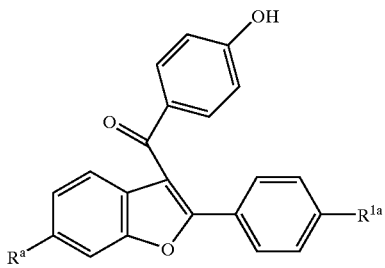

wherein $R^a$ and $R^{1a}$ are as defined above. The ether form of compounds of formula II is then produced by the substitution of the hydrogen on the hydroxy group by an alkyl group.

The last step in preparing starting materials of formula II via the present process involves alkylating the selectively dealkylated compound of formula VII with an appropriate alkylation agent of formula VIII below, essentially as described in Preparation 5B, infra.

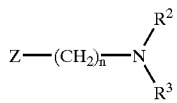

wherein Z is a leaving group such as chloro or bromo, and n, $R^2$, and $R^3$ are as defined above.

This reaction usually employs equimolar to a slight excess of a formula VIII compound relative to the formula VII substrate. The reaction is performed in a non-reactive solvent such as N,N-dimethylformamide and the like, in the presence of a base such as, for example, potassium carbonate. The reaction is performed at temperatures from about 80° C. to about 120° C. and allowed to run until compounds of formula II are prepared. The reaction typically takes about 1 hour when run at 100° C. However, the progress of the reaction may be monitored by using standard chromatographic techniques.

Preferred formula II starting materials are those in which n is 2, and $R^2$ and $R^3$ are methyl or ethyl, or $R^2$ and $R^3$ are combined to form a pyrrolidino moiety or a piperidino moiety. Of these, combining $R^2$ and $R^3$ to form a piperidino moiety is especially preferred.

Compounds of formula IX generally are prepared by adding a formula II compound, or, preferably, the hydrochloride salt thereof, to an appropriate solvent, and reacting the resulting mixture with a reducing agent such as, for example, lithium aluminum hydride (LAH), under an inert gas such as nitrogen. The amount of reducing agent used in this reaction is an amount sufficient to reduce the carbonyl group of a formula II compound to form a carbinol of formula IX below. Generally, a liberal excess of the reducing agent per equivalent of the substrate is used.

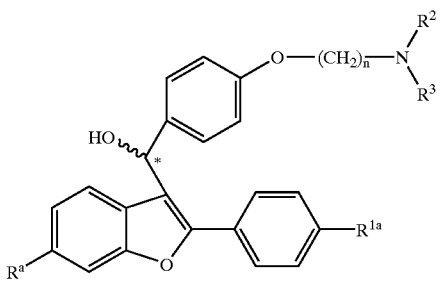

IX wherein $R^a$, $R^{1a}$, $R^2$, $R^3$, and n of formula IX are as defined above, or a salt thereof.

Appropriate solvents include any solvent or mixture of solvents which will remain inert under reducing conditions. Suitable solvents include ether, dioxane, and tetrahydrofuran (THF).

The temperature employed in this step is that which is sufficient to effect completion of the reduction reaction. Ambient temperature, in the range from about 17° C. to about 25° C., generally is adequate.

The length of time for this step is that amount necessary for the reaction to occur. Typically, this reaction takes from about 1 to about 20 hours. The optimal time can be determined by monitoring the progress of the reaction via conventional chromatographic techniques.

Optionally, the $C_1$–$C_4$ alkoxy moieties of a formula IX compound may be dealkylated, via standard procedures, prior to further reduction as described below. The resulting diphenolic compounds of formula IXa are considered to be part of the present invention

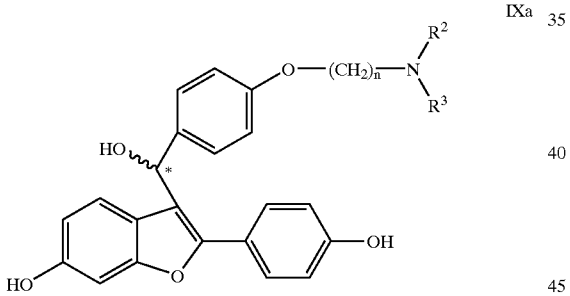

IXa wherein $R^2$, $R^3$, and n are as defined above.

The carbinol products from this reaction are extracted essentially via the method described in Example 1, infra, are novel, and are useful intermediates for the preparation of formula I compounds of the present invention by further reduction.

In formula IX, the carbon atom designated "*" is an asymmetric center. Thus, these compounds can have an R- or S-configuration, or a mixture thereof. Both enantiomers are considered to be part of the present invention.

Once a carbinol of the present invention is prepared, one option is to further reduce such a carbinol via standard procedures, to give a compound of formula I.

Typically a carbinol of formula IX is suspended in an appropriate solvent and cooled under an inert gas such as nitrogen. To this suspension is added a suitable trialkyl silane reducing agent, preferably triethyl silane, and a reasonably strong protic acid such as hydrochloric acid, trifluoracetic acid, and the like.

Appropriate solvents can be any solvent or mixture of solvents which remain inert under the reaction conditions employed in the process. For example, halogenated alkane solvents such as dichloromethane and 1,2-dichloroethane, as well as haloaromatics such as chlorobenzene and the like may be used. Of these, dichloromethane is preferred.

The temperature employed in this step is that which is sufficient to effect completion of the present reduction process. Typically, the reaction is cooled to about 0° C. and the reaction solution is kept on ice until the reaction is complete; however, ambient temperature also is satisfactory. In general, this reaction is completed in less than three hours, and the progress of the reaction can be monitored via standard techniques.

In particular cases, when phenolic hydroxys are present in the compounds of formula IXa, the use of triethylsilyl as a reducing agent can lead to the formation of the silyl adduct of the phenol. On occasion, this adduct can be isolated as seen in Example 2. In other cases, traces of such silylated phenols can be seen as minor impurities. The intermediate methylene free bases which contain such impurities are cleaved to the free phenol when the compounds are converted to their hydrochloride salts, as seen in Example 3, infra.

Alternatively, a novel process may be used to prepare compounds of formula Ia of the present invention by reducing a ketone of formula II above. This process is shown below in Scheme I.

Scheme I

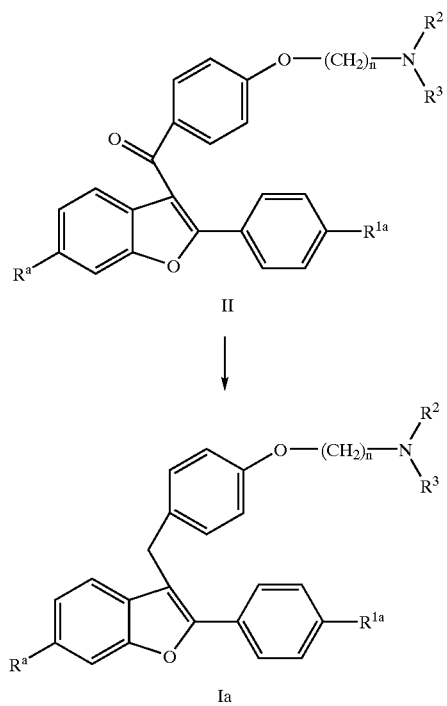

wherein
$R^a$, $R^{1a}$, $R^2$, $R^3$, and n are as defined above, or a pharmaceutically acceptable salt thereof.

In this process, a formula II compound, or a salt thereof, is optionally dealkylated and then reacted with a reducing agent such as lithium aluminum hydride in the presence of a solvent having a boiling point in the range from about 150° C. to about 200° C. The reaction product of this reduction step can then optionally be salified via standard procedures. Alternatively, the reduction step of the present process may first be carried out, followed by the optional dealkylation step. Preferably, each step of this novel process is carried out in separate vessels, but it is possible to carry out each step of the present process in the same vessel.

The amount of reducing agent used in this reaction is an amount sufficient to reduce the carbonyl group of a formula II compound to form a compound of formula I. Generally, a generous excess of the reducing agent per equivalent of the substrate is used.

The solvent used in the present process is required to have a relatively high boiling point, in the range from about 150° C. to about 200° C., as represented by solvents such as, for example n-propylbenzene, diglyme (1,1'-oxybis[2-methoxyethane]), and anisole, and Red-Al® {[sodium bis (2-methoxyethoxylaluminum hydride)]} which also is used as the reducing agent. Of these, n-propylbenzene is the preferred solvent with formula II compounds as shown above. The alkoxy substituents of compounds of formula II may first be dealkylated, to form a diphenol compound via standard procedures herein described, which can then be reduced via the present, novel process to provide formula I compounds. In this instance, Red-Al is the preferred reducing agent.

The temperature used in this reaction is that which is sufficient to complete the reduction reaction. Preferably, the reaction mixture is heated to reflux for about 15 minutes to about 6 hours, and allowed to cool to ambient temperature. A small amount of deionized water is added to the mixture followed by the addition of a small aliquot of 15% sodium hydroxide: deionized water (w/w). The mixture is stirred until the reaction is complete. The optimal amount of time for this reaction to run, typically from about 10 minutes to about 1 hour, can be determined by monitoring the progress of the reaction via standard techniques.

The formula I products from this reduction reaction are extracted essentially as described in Example 7, infra.

Formula I compounds in which R and $R^1$ are —OH and/or —O($C_1$-$C_4$ alkyl) are novel and can be used as pharmaceutically active agents for the methods herein described, or can be derivalitized to provide other novel compounds of formula I which also are useful for the present methods.

For example, when R and/or $R^1$ are —O($C_1$-$C_4$ alkyl), (thus, not having been dealkylated as one above option provides), such groups can be removed via standard dealkylation techniques to prepare an especially preferred compound of formula I.

Other formula I compounds are prepared by replacing the newly formed R and $R^1$ hydroxy groups with a moiety of the formula —O—CO—($C_1$-$C_6$ alkyl), —O—CO—Ar in which Ar is optionally substituted phenyl, or —O—$SO_2$—($C_4$-$C_6$ alky) via well known procedures. See, e.g., U.S. Pat. No. 4,358,593, supra.

For example, when a —O—CO($C_1$-$C_6$ alkyl) or —O—CO—Ar group is desired, the dihydroxy compound of formula I is reacted with an agent such as acyl chloride, bromide, cyanide, or azide, or with an appropriate anhydride or mixed with anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminepyridine or 4-pyrrolidinopyridine may be used. See, e.g., Haslam, et al., *Tetrahedron*, 3:2409–2433 (1980).

The acylation reactions which provide the aforementioned R and $R^1$ groups are carried out at moderate temperatures in the range from about −25° C. to about 100° C., frequently under an inert atmosphere such as nitrogen gas. However, ambient temperature is usually adequate for the reaction to run.

Such acylations of the hydroxy group also may be performed by acid-catalyzed reactions of the appropriate carboxylic acids in inert organic solvents or heat. Acid catalysts such as sulfuric acid, polyphosphoric acid, methanesulfonic acid, and the like are used.

The aforementioned R and $R^1$ groups also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —O—CO—($C_1$-$C_6$ alkyl) and —O—CO—Ar groups are carried out in solvents as discussed above. These techniques which do not produce an acid product in the course of the reaction, of course, do not call for the use of an acid scavenger in the reaction mixture.

When a formula I compound is desired in which R and $R^1$ is —O—$SO_2$—($C_4$-$C_6$ alkyl), the formula I dihydroxy compound is reacted with, for example, a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride. Such reactions are carried out under conditions such as were explained above in the discussion of reaction with acid halides and the like.

Compounds of formula I can be prepared so that R and $R^1$ bear different biological protecting groups or, preferably, are prepared so that R and $R^1$ each bear the same biological protecting group. Preferred protecting groups include —$OCH_3$, —O—CO—C($CH_3$)$_3$, —O—CO—$C_6H_5$, and —O—$SO_2$—($CH_2$)$_3$—$CH_3$.

The term "biological protecting groups" refers to those R and $R^1$ substituents which delay, resist, or prohibit removal of such groups in a biological system such as, for example, following administration of a formula I compound containing the above-described R and $R^1$ groups to a human. Such compounds of formula I also are useful for the methods herein described.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2- benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

Likewise, salts of formula IX also can be prepared by the procedures discussed above.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

The terms "NMR", "IR" or "MS" following a synthesis protocol indicates that the nuclear magnetic resonance spectrum, infrared spectrum, or the mass spectrometry was performed and was consistent with the title product.

PREPARATION 1

2-(3-Methoxyphenoxy)-1-(4-methoxyphenyl)ethanone

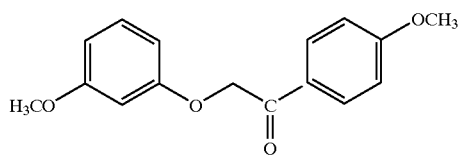

In a one liter round-bottom flask, fitted with a condenser and nitrogen inlet, were added 3-methoxyphenol (12.4 g, 0.1 mole), 4-methoxyphenacyl bromide (22.9 g, 0.1 mole), potassium carbonate (17.3 g, 0.125 mole) in 100 ml of 2-butanone. This mixture was heated to 80° C. and was maintained at this temperature for about four hours. The progress of the reaction was monitored by thin layer chromatography (silica gel, 9:1 toluene:ethyl acetate).

After the four hours at 80° C. the reaction mixture was cooled and the reaction mixture was partitioned by the addition of water. The organic phase was removed and the aqueous layer was washed with 2-butanone. The organic layers were then combined, dried over magnesium sulfate, and the solvents were removed in vacuo to yield 31.1 grams of a yellow oil. The yellow oil was further purified by chromatography, the fractions containing the desired product were then crystallized. All of the crystalline fractions were combined and then dissolved in 80 ml of hot ethanol. Fifteen milliliters of hot water was then added, the product was crystallized, and subsequently washed with an ethanol/water mixture to yield 19.1 g (70%) of the desired title product. mp 52.5°–53.5° C.

Analysis for the title compound: Theory: C, 68.08; H, 5.71; N, 2.84. Found: C, 67.86; H, 5.51; N, 2.88.

PREPARATION 2

2-4'-Methoxyphenyl-6-methoxybenzofuran

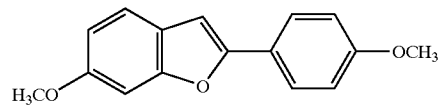

The cyclization-rearrangement of the product of Preparation 1 was performed essentially as described in C. Goldenberg, et al., *Chimie Therapeutique*, 398: 411 (1973). In a 500 ml 3-neck round bottom flask polyphosphoric acid (30 g) was added to 200 ml of xylene. The mixture was then heated to about 120° C. To this heated mixture was then added 2-(3-methoxyphenoxy)-1-(4-methoxyphenyl)ethanone (10 g, 0.037 mole), ,prepared as described supra, and the temperature was raised to about 170° C., and maintained at that temperature for about eight hours. The reaction mixture was then cooled and water was added.

The dark aqueous layer was separated from the yellow organic phase. The organics were washed with water and by aqueous sodium carbonate, and then dried over anhydrous magnesium sulfate. The solvents were removed in vacuo, resulting in a yellow-orange solid. The product was recrystallized from a minimum of hot acetone, followed by the addition of ethanol and water. The residual acetone was removed by boiling. Cooling to room temperature yielded white crystals (2.09 g, 22% yield). mp 158° C.

Analysis for the title compound: Theory: C, 75.58; H, 5.55; O, 18.88. Found: C, 75.33; H, 5.67; O, 18.62.

PREPARATION 3

[2-(4-Methoxyphenyl)-6-methoxybenzofuran-3-yl][4-methoxyphenyl]methanone

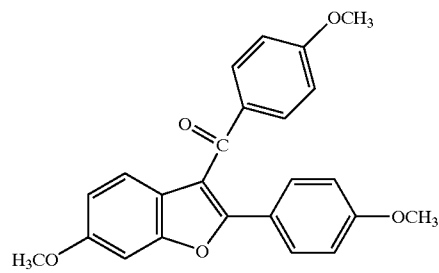

In a 250 ml 3-neck round bottom flask were added 2-hydroxy-4-methoxybenzaldehyde (10 g, 65.7 mmoles), 1-(4-methoxyphenyl)-2-(4-methoxyphenyl)ethanone (16 g, 62.6 mmoles), ethyl acetate (100 ml) and ethanol (25 ml). The reaction mixture was then warmed to about 45° C. until all the starting materials were dissolved. Hydrogen chloride gas was then bubbled in for about 30 minutes, resulting in the formation of a bright red coloration. The reaction was

PREPARATION 5

[2-(4-Methoxyphenyl)-6-methoxybenzofuran-3-yl]
[4-(2-(1-piperidinyl)ethoxy]phenyl]methanone

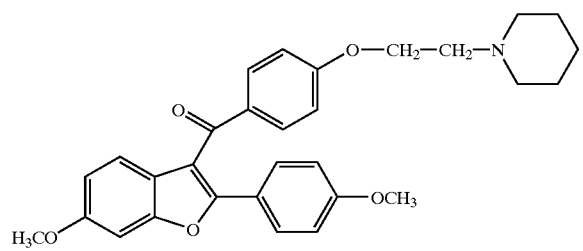

Method A:

Acylation of 2-4'-methoxyphenyl-6-methoxybenzofuran 4-[2-(Piperidin-1-yl)ethoxy]benzoyl chloride (0.562 g, 1.96 mmoles) was added to ethylene chloride (20 ml), followed by the addition of 2-4'-methoxyphenyl-6-methoxybenzofuran (0.500 g, 1.96 mmoles), prepared as described in Preparation 2, supra. This mixture was stirred at room temperature as aluminum trichloride (1.96 g, 14.7 mmoles) was added. This reaction mixture was then stirred overnight.

The reaction mixture was then poured over ice, and extracted with warm chloroform (3×50 ml). The chloroform was removed by evaporation. Sodium carbonate, water and ethyl acetate were then added and the organic layer was removed, dried over magnesium sulfate, and the solvents were removed in vacuo to provide a yellow oil. The desired product was further purified by chromatography of the yellow oil to yield the desired title product.

Analysis for the title compound: Theory: C, 74.21; H, 6.44; N, 2.88; O, 16.47. Found: C, 74.11; H, 6.71; N, 2.75; O, 16.57.

Method B:

Alkylation of [2-(4-methoxyphenyl)-6-methoxybenzofuran-3-yl][4-hydroxyphenyl]methanone In 100 ml of anhydrous N,N-dimethylformamide in a 500 ml round bottom flask were added [2-(4-methoxyphenyl)-6-methoxybenzofuran-3-yl][4-hydroxyphenyl]methanone (10.50 g, 28 mmoles), prepared as described in Preparation 4, supra, and potassium carbonate (6.20 g, 34 mmoles). This mixture was heated to 100° C. and then N-2-chloroethyl piperidine (6.20 g, 34 mmoles) was added gradually. The reaction mixture was kept at 100° C. for about one hour.

The N,N-dimethylformamide was removed under reduced pressure and the residue was dissolved in ethyl acetate and water. The ethyl acetate layer was removed and the aqueous layer was washed with more ethyl acetate. The organic fractions were combined, dried over magnesium sulfate, and the solvents were removed in vacuo, yielding 13.3 g of a yellow oil which crystallized upon standing. The product was recrystallized from methanol which was cooled to −30° C. prior to filtration, yielding 11.4 g (84%) of the desired product as pale yellow crystals. mp 87–89° C.

Analysis for the title compound: Theory: C, 74.21; H, 6.44; N, 2.88; O, 16.47. Found: C, 74.31; H, 6.34; N, 2.63; O, 16.47.

then allowed to stand at room temperature for about two hours at which time the solvents were removed in vacuo to leave a bright red oil.

The red oil was dissolved in 180 ml of methanol and 30 ml of 20% sulfuric acid was added with stirring and cooling. Hydrogen peroxide (30 ml) was added dropwise and the mixture was allowed to stir for about 30 minutes. A saturated sodium chloride solution (500 ml) and ethyl acetate (300 ml) were added to the reaction mixture and the organic fraction was removed. The organic layer was washed with a saturated sodium chloride solution, dried, and the solvents were removed in vacuo to provide 25 g of a reddish brown oil which was further purified by chromatography to yield the title product (1.25 g) as a yellow oil. mp 106–109° C.

Analysis for the title compound: Theory: C, 74.21; H, 5.19; O, 20.60. Found: C, 74.07; H, 5.22; O, 20.38.

PREPARATION 4

[2-(4-Methoxyphenyl)-6-methoxybenzofuran-3-yl]
[4-hydroxyphenyl]methanone

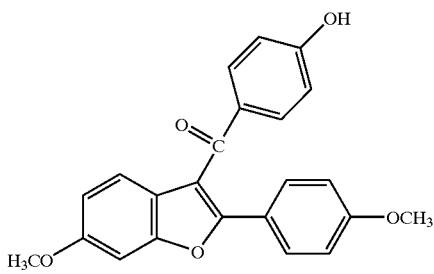

In a three-neck round bottom flask under a nitrogen atmosphere and cooled in an ice bath, ethanethiol (0.95 ml, 1.288 mmoles) was dissolved in 10 ml of anhydrous N,N-dimethylformamide. To this solution was added n-butyllithium (0.60 ml of a 1.6 M in hexane solution, 0.966 mmole) followed by the addition of [2-(4-methoxyphenyl)-6-methoxybenzofuran-3-yl][4-hydroxyphenyl]methanone (250 mg, 0.644 mmole), prepared as described in Preparation 3, supra. The reaction mixture was then heated to 80° C. and allowed to remain at that temperature for about 16 hours.

The reaction mixture was then poured into 1 N hydrochloric acid and extracted with ethyl acetate. The organic layer was then washed with a saturated sodium chloride solution, dried over magnesium sulfate, filtered and the solvents were removed in vacuo. The desired product was further purified by column chromatography. The product was then crystallized from methanol yielding 130 mg (81%) of the desired product. mp 148–149° C.

Analysis for the title compound: Theory: C, 73.79; H, 4.85; O, 21.37. Found: C, 73.68; H, 5.12; O, 21.17.

PREPARATION 6

[2-(4-Hydroxyphenyl)-6-hydroxybenzofuran-3-yl]
[4-[2-(1-piperidinyl)ethoxy]phenyl]methanone

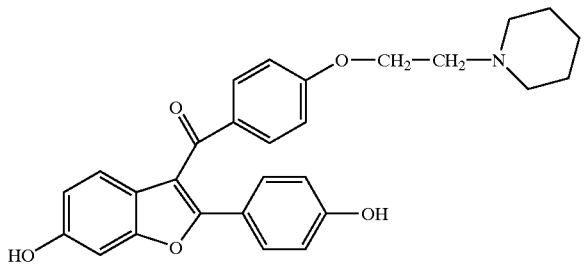

The title product was prepared by the demethylation of the product of preparation 5, supra. In a 250 ml three-neck round bottom flask were combined 1,2-dichloroethane (50 ml) and aluminum trichloride (9.60 g, 72 mmoles) and ethanethiol (6.39 g, 103 mmoles) to provide a pale yellow solution. To this liquid was then added the product of Example 1 (5.00 g, 10.3 mmoles) in a gradual fashion. A red oil precipitated and the mixture was stirred for about 20 minutes. After cooling the reaction mixture in an ice bath, 100 ml of tetrahydrofuran was added and the mixture was allowed to stir until all of the oil had gone into solution.

The reaction mixture was then poured over ice (200 ml) and water (500 ml) and concentrated hydrochloric acid (10 ml) were added. The oil which precipitated was separated from the liquid by decantation. The liquid was extracted with chloroform (warm, 2×300 ml). The oil was dissolved by mixing with ethyl acetate, chloroform, sodium bicarbonate, and a small amount of sodium hydroxide. The chloroform extract and the ethyl acetate-chloroform solution containing the dissolved oil were combined and transferred to a separatory funnel. The organic phase was washed with sodium bicarbonate, dried over magnesium sulfate, and the solvents were removed under reduced pressure to yield a yellow foam, which was further purified by high performance liquid chromatography.

EXAMPLE 1

[2-(4-Hydroxyphenyl)-6-hydroxybenzofuran-3-yl]
[4-[2-(1-piperidinyl)ethoxy]phenyl]methanol

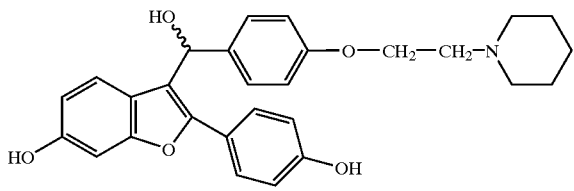

4.57 g (0.01 mol) of [2-(4-hydroxyphenyl)-6-hydroxybenzofuran-3-yl][4-[2-(1-piperidinyl)ethoxy] phenyl]methanone was dissolved in 250 mL of THF and 2 g (0.053 mol) of LiAlH$_4$ was slowly added over a period of twenty minutes to the stirring solution. The reaction mixture was stirred and kept under a nitrogen atmosphere and the reaction was allowed to proceed for eighteen hours at room temperature and then it was concentrated to dryness in vacuo. 500 mL of EtOAc was slowly added along with 2 mL of water. After stirring for 10 minutes, 500 mL of water was added and the EtOAc layer was removed. The EtOAc layer was washed with an additional 500 mL of water and the layers were separated. The EtOAc layer was dried with anhydrous Na$_2$SO$_4$ and concentrated to dryness to yield 2.66 g of the title compound as tan amorphous powder.

$^1$HNMR: Consistent with the proposed structure. MS: m/e=460 (M+1) FD; C$_{28}$H$_{29}$NO$_5$.

EXAMPLE 2

[2-(4-Triethyloilyloxyphenyl)-6-hydroxybenzofuran-3-yl][4-[2-(1-piperidinyl)ethoxy]phenyl]methane

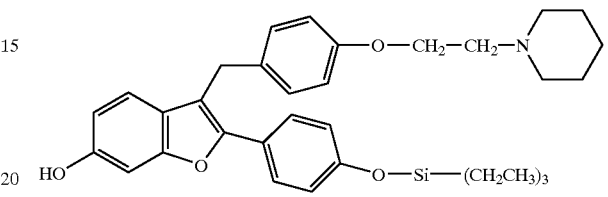

1.69 g (0.0036 mol) of 2-(4-hydroxyphenyl)-6-hydroxybenzofuran-3-yl][4-[2-(1-piperidinyl)ethoxy] phenyl]methanol was dissolved in 25 mL of CH$_2$Cl$_2$ and 470 mg (0.004 mol) of triethyl silane was added. The reaction mixture was stirred under a nitrogen atmosphere. 25 mL of trifluoroacetic acid was added. The reaction was allowed to proceed at room temperature for six hours. The reaction was terminated by evaporating the volatiles in vacuo. 200 mL of saturated NaCO$_3$ solution was added and extracted (3×) with 100 mL portions of EtOAc. The combined EtOAc extracts were washed with water and dried by filtration through anhydrous Na2SO$_4$ and the reaction mixture was evaporated to dryness. This yielded 690 mg of the title compound as a tan amorphous powder.

PMR: Consistent with the proposed structure (one —SiEt$_3$); MS: m/e=558 (M+1) and 444 (M-Et$_3$Si) FD.

EXAMPLE 3

[2-(4-Hydroxyphenyl)-6-hydroxybenzofuran-3-yl]
[4-[2-(1-piperidinyl)ethoxy]phenyl]methane
Hydrochloride

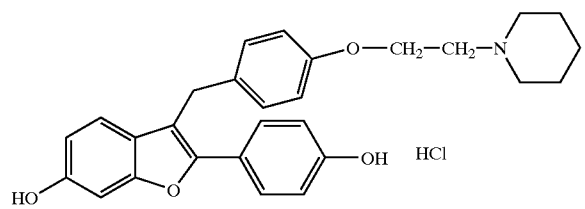

650 mg of [2-(4-triethylsilyloxyphenyl)-6-hydroxybenzofuran-3-yl][4-[2-(1-piperidinyl)ethoxy] phenyl]methane was dissolved in 50 mL of methylene chloride and 5 mL of methanol. 25 mL of a saturated solution of ethyl ether-hydrochloric acid was added. The reaction mixture was evaporated to dryness. This yielded 550 mg of the title compound as a light pink amorphous powder. PMR: Consistent with the proposed structure (no Et$_3$Si— group)

Analysis for the title compound: Theory: C, 70.06; H, 6.30; N, 2.92. Found: C, 69.86: H, 6.48; N, 2.66. C$_{28}$H$_{29}$NO$_4$.HCl MS m/e=444(M–HCl)FD.

EXAMPLE 4

[2-(4-Methoxyphenyl)-6-methoxybenzofuran-3-yl]
[4-[2-(1-piperidinyl)ethoxy]phenyl]methanol

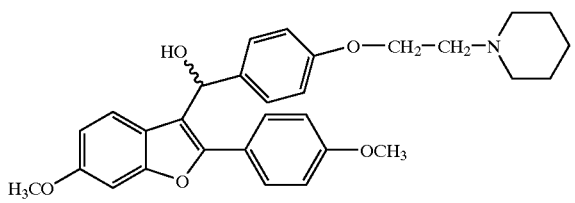

This compound was prepared in a manner similar to that in Example 1, starting with 2 g (4.13 mmol) of [2-(4-methoxyphenyl)-6-methoxybenzofuran-3-yl][4-[2-(1-piperidinyl)ethoxy]phenyl]methanone and obtaining 1.66 g of the title compound as a tan amorphous powder.

$^1$HNMR: Consistent with the proposed structure. MS: m/e=487 (M+) FD; Analysis for the title compound: Theory: C, 73.90; H, 6.82; N, 2.87. Found: C, 73.66; H, 6.88; N, 3.06.

EXAMPLE 5

[2-(4-Methoxyphenyl)-6-methoxybenzofuran-3-yl]
[4-[2-(1-piperidinyl)ethoxy]phenyl]methane

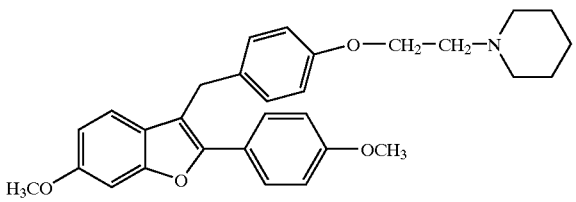

This compound was prepared in a manner similar to that in Example 2, starting with 1.64 g (3.36 mmol) of the carbinol from Example 4 and obtaining 680 mg of the title compound as a tan amorphous powder.

$^1$HNMR: Consistent with the proposed structure. MS: m/e=471 (M+) FD; $C_{30}H_{33}NO_4$.

EXAMPLE 6

[2-(4-Methoxyphenyl)-6-methoxybenzofuran-3-yl]
[4-[2-(1-piperidinyl)ethoxy]phenyl]methane
Hydrochloride

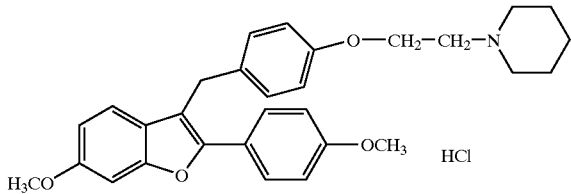

This compound was prepared in the same manner as Example 3, the final product was crystallized from ethyl acetate-methanol. 680 mg of the starting free base yielded 320 mg of the final salt.

$^1$HNMR: Consistent with the proposed structure. Analysis for the title compound: Theory: C, 70.92; H, 6.74; N, 2.76. Found: C, 70.76; H, 6.79; N, 2.75.

EXAMPLE 7

[2-(4-Methoxyphenyl)-6-methoxybenzofuran-3-yl]
[4-[2-(1-piperidinyl)ethoxy]phenyl]methane
Hydrochloride

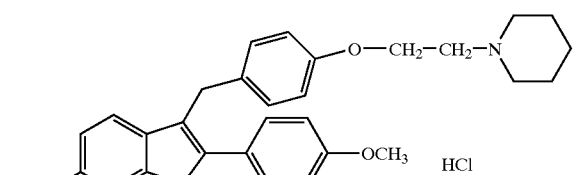

500 mg (12.52) mmol) of 95% lithium aluminum hydride and 500 mg (1.03 mmol) [2-(4-methoxyphenyl)-6-methoxybenzofuran-3-yl][4-[2-(1-piperidinyl)ethoxy]phenyl]methanone in 20 mL of n-propyl benzene were heated to reflux one hour and then allowed to cool to room temperature. To the mixture was carefully added 1 mL of deionized water followed by 3 mL of 15% (w/w) sodium hydroxide/deionized water and then another 1 mL deionized water. The mixture was stirred for 15 minutes at ambient temperature and the resulting precipitate was removed by vacuum filter. The mother liquor was then diluted with methylene chloride (100 mL), washed once with brine, dried on sodium sulfate, and then retovaped to dryness. The clear gum was purified by radial chromatography on a 4 mm plate and 19:1 methylene chloride:methanol as eluent. The clear gum was taken up in a minimal amount of methanol and then a saturated solution of methanol/hydrochloric acid (g) was added. Product crystallized from methanol to yield 230 mg of off-white amorphous material (47% yield).

Analysis for title compound: Theory: C, 70.92; H, 6.75; N, 2.76. Found: C, 70.69; H, 6.53; N, 2.88.

EXAMPLE 8

[2-(4-Hydroxyphenyl)-6-hydroxybenzofuran-3-yl]
[4-[2-(1-hexamethyleneimine)ethoxy]phenyl]
methanol

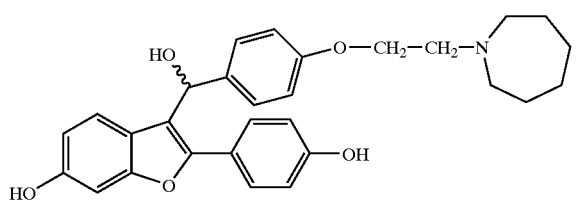

1.524 g (3mmol) of [2-(4-hydroxyphenyl)-6-hydroxybenzofuran-3-yl][4-[2-(1-hexamethyleneimine)ethoxy]phenyl]methanone hydrochloride salt was converted to 830 mg of the title compound through the process described in Example 1.

$^1$HNMR: Consistent with the proposed structure MS: m/e=474 (M+1) FD; $C_{29}H_{31}NO_5$.

EXAMPLE 9

[2-(4-Hydroxyphenyl)-6-hydroxybenzofuran-3-yl][4-[2-(1-hexamethyleneimine)ethoxy]phenyl]methane

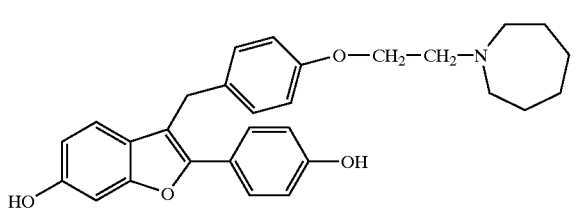

800 mg (1.7 mmol) of the product of Example 8 was converted to 700 mg of the title compound by the process described in Example 2.

MS: m/e=458 (M+1) FD; $C_{29}H_{31}NO_4$.

EXAMPLE 10

[2-(4-Hydroxyphenyl)-6-hydroxybenzofuran-3-yl][4-[2-(1-hexamethyleneimine)ethoxy]phenyl]methane Hydrochloride

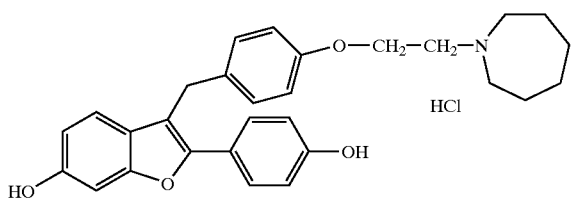

700 mg of the compound from Example 9 was converted to its hydrochloride by the method described in Example 3. This yielded 300 mg of the title compound as a white amorphous powder.

¹HNMR: Consistent with the proposed structure. MS: m/e=457 (M−HCl) FD; Analysis for the title compound: Theory: C, 70.51; H, 6.53; N, 2.84. Found: C, 70.23; H, 6.53; N, 2.95.

EXAMPLE 11

[2-(4-Hydroxyphenyl)-6-hydroxybenzofuran-3-yl][4-[2-(1-pyrrolidinyl)ethoxy]phenyl]methanol

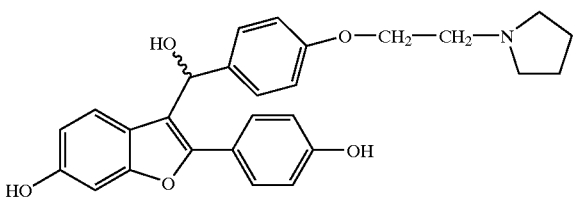

1.38 g (3 mmol) of [2-(4-hydroxyphenyl)-6-hydroxybenzofuran-3-yl][4-[2-(1-pyrrolidenyl)ethoxy]phenyl]methanone was reduced to the carbinol by the method described in Example 1. This yielded 550 mg of the title compound as an amorphous powder.

¹HNMR: Consistent with the proposed structure. MS: m/e=462 (M+1) FD; $C_{27}H_{27}NO_5$.

EXAMPLE 12

[2-(4-Hydroxyphenyl)-6-hydroxybenzofuran-3-yl][4-[2-(1-pyrrolidinyl)ethoxy]phenyl]methane

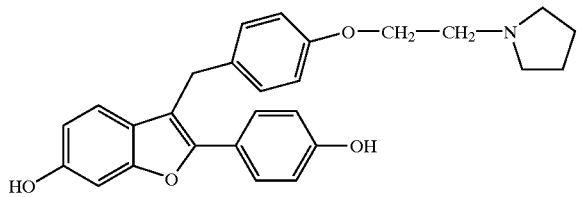

550 mg (1.2 mmol) of the product of Example 11 was reduced to the methane by the method described in Example 2. This yielded 270 mg of the title compound as an amorphous powder.

¹HNMR: Consistent with the proposed structure. MS: m/e=446 (M+1) FD; $C_{27}H_{27}NO_4$.

EXAMPLE 13

[2-Phenyl-6-hydroxybenzofuran-3-yl][4-[2-(1-piperidinyl)ethoxy]phenyl]methanol

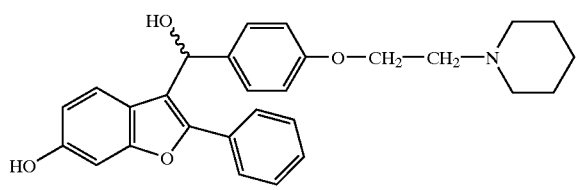

2000 mg (4.1 mmol) of [2-phenyl-6-hydroxybenzofuran-3-yl][4-[2-(1-piperidinyl)ethoxy]phenyl]methanone hydrochloride was reduced by the method described in Example 1. This yielded 1.31 g of the title compound as an amorphous powder.

¹HNMR: Consistent with the proposed structure. MS: m/e=443 (M) FD; Analysis for the title compound: Theory: C, 75.82; H, 6.59; N, 3.16. Found: C, 75.14; H. 6.88; N, 3.03.

EXAMPLE 14

[2-Phenyl-6-hydroxybenzofuran-3-yl][4-[2-(1-piperidinyl)ethoxy]phenyl]methane

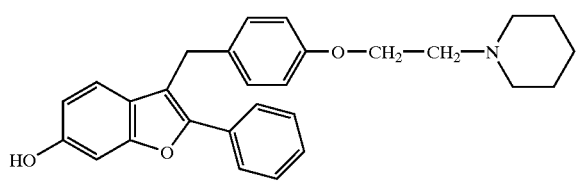

1.3 g (2.9 mmol) of the carbinol from Example 13 was reduced in the manner described in Example 2. This yielded 1.23 g of the title compound as an amorphous powder.

¹HNMR: Consistent with the proposed structure. MS: m/e=428 (M+1) and small peak of 542 indicating a small amount of the 6-triethylsilyloxy derivative. $C_{28}H_{29}NO_4$.

EXAMPLE 15

[2-Phenyl-6-hydroxybenzofuran-3-yl][4-[2-(1-piperidinyl)ethoxy]phenyl]methane Hydrochloride

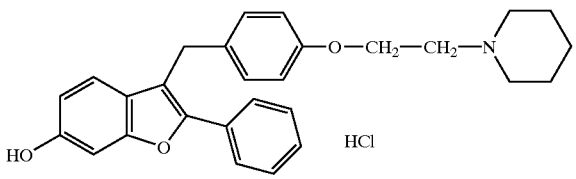

1.23 g of the free base derived in Example 14 was converted to its hydrochloride salt in the manner exemplified in Example 3. This yielded 720 mg of the title compound as a white amorphous powder.

$^1$HNMR: Consistent with the proposed structure. MS: m/e=429 (M−HCl) FD; Analysis for the title compound: Theory: C, 72.48; H, 6.52; N, 3.02. Found: C, 72.18; H, 6.73; N, 2.78.

EXAMPLE 16

[2-(4-Hydroxyphenyl)-benzofuran-3-yl][4-[2-(1-piperidinyl)ethoxy]phenyl]methanol

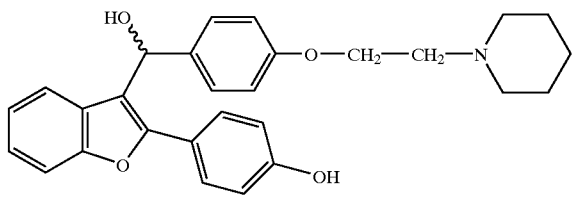

2.0 g (4.23 mmol) of [2-(4-hydroxyphenyl)-benzofuran-3-yl][4-[2-(1-piperidinyl)ethoxy]phenyl]methanone hydrochloride was reduced to the carbinol using the method described in Example 1. This yielded 1.59 g of the title compound as an amorphous powder.

$^1$HNMR: Consistent with the proposed structure. MS: m/e=444 (M+1) FD; Analysis for the title compound: Theory: C, 75.82; H, 6.59; N, 3.16. Found: C, 75.34; H, 6.93; N, 3.02.

EXAMPLE 17

[2-(4-Hydroxyphenyl)-benzofuran-3-yl][4-[2-(1-piperidinyl)ethoxy]phenyl]methanol

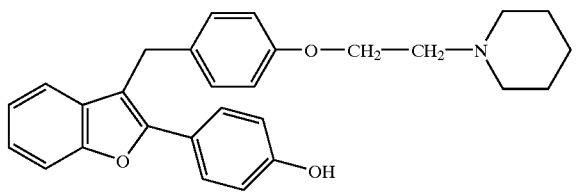

1.5 g (3.38 mmol) of the carbinol in Example 16 was further reduced to the methane derivative as described in Example 2. This yielded 1.29 g of the title compound as an amorphous solid.

$^1$HNMR: Consistent with the proposed structure. MS: m/e=428 (M+1) and a small peak at 542 which is the triethylsilyloxy derivative on the phenol. $C_{28}H_{29}NO_3$.

EXAMPLE 18

[2-(4-Hydroxyphenyl)-benzofuran-3-yl][4-[2-(1-piperidinyl)ethoxy]phenyl]methane Hydrochloride

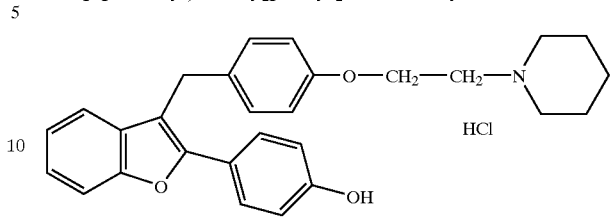

1.2 g of the free base synthesized in Example 17 was converted to the hydrochloride salt in a manner described in Example 3. This yielded 810 mg of the title compound as an amorphous solid.

$^1$HNMR: Consistent with the proposed structure. MS: m/e=428 (M−HCl) FD; Analysis for the title compound: Theory: C, 72.48; H, 6.52; N, 3.02. Found: C, 71.95; H, 6.67; N, 2.78.

EXAMPLE 19

[2-(4-Methoxyphenyl)-6-methoxybenzofuran-3-yl][4-[2-dimethylaminoethoxy]phenyl]methanol

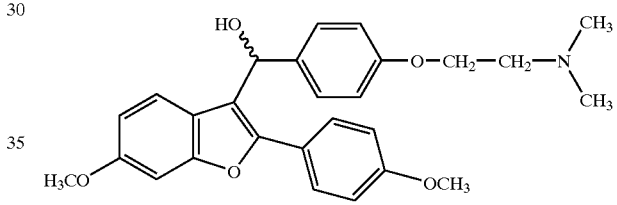

1.335 g (3 mmol) of [2-(4-methoxyphenyl)-6-methoxybenzofuran-3-yl][4-[2-dimethylaminoethoxy]phenyl]methanone was reduced to the carbinol by the method described in Example 1. This yielded 920 mg of the title compound as an oil.

$^1$HNMR: Consistent with the proposed structure. MS: m/e=448 (M+1) FD; $C_{27}H_{29}NO_5$.

EXAMPLE 20

[2-(4-Methoxyphenyl)-6-methoxybenzofuran-3-yl][4-[2-dimethylaminoethoxy]phenyl]methane

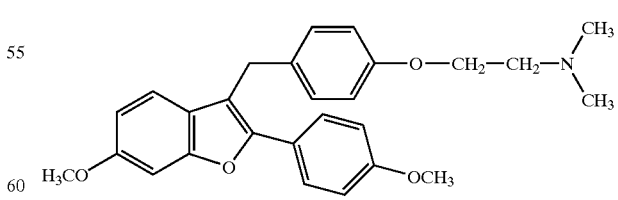

890 mg (2 mmol) of the carbinol in Example 19 was reduced in the manner described in,Example 2. This yielded 640 mg of the title compound as an oil.

MS: m/e=432 (M+1) FD; $C_{27}H_{29}NO_4$.

EXAMPLE 21

[2-(4-Methoxyphenyl)-6-methoxybenzofuran-3-yl]
[4-[2-dimethylaminoethoxy]phenyl]methane
Hydrochloride

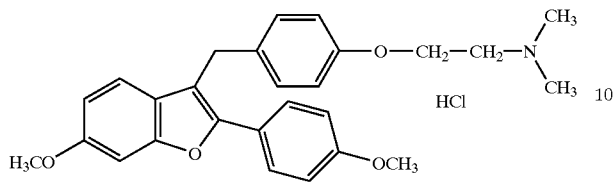

800 mg of the free base in Example 20 was converted to its hydrochloride salt in the manner described in Example 3. This yielded 570 mg of the title compound as an amorphous solid.

$^1$HNMR: Consistent with the proposed structure. MS: m/e=431 (M–HCl) FD; Analysis for the title compound: Theory: C, 69.29; H, 6.46; N, 2.99. Found: C, 68.83; H, 6.77; N, 3.47.

EXAMPLE 22

[2-(4-Methoxyphenyl)-6-methoxybenzofuran-3-yl]
[4-[2-diethylaminoethoxy]phenyl]methanol

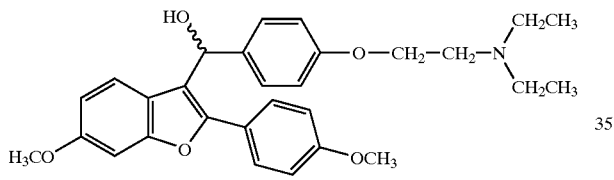

1.420 g (3 mmol) of [2-(4-methoxyphenyl)-6-methoxybenzofuran-3-yl][4-[2-diethylaminoethoxy]phenyl]methanone was reduced to the carbinol by the method described in Example 1. This yielded 1.07 g of the title compound as an oil.

$^1$HNMR: Consistent with the proposed structure. MS: m/e=475 (M) FD; $C_{29}H_{33}NO_5$.

EXAMPLE 23

[2-(4-Methoxyphenyl)-6-methoxybenzofuran-3-yl]
[4-[2-diethylaminoethoxy]phenyl]methane

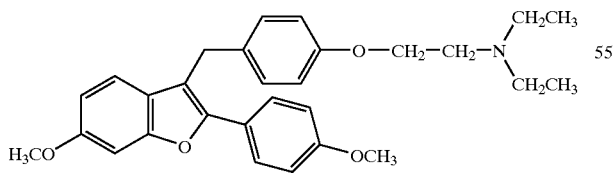

1.070 g (2.25 mmol) of the carbinol from Example 22 was reduced by the method described in Example 2. This yielded 800 mg of the title compound as an oil.

$^1$HNMR: Consistent with the proposed structure. MS: m/e=459 (M) FD; $C_{29}H_{33}NO_4$.

EXAMPLE 24

[2-(4-Methoxyphenyl)-6-methoxybenzofuran-3-yl]
[4-[2-diethylaminoethoxy]phenyl]methane
Hydrochloride

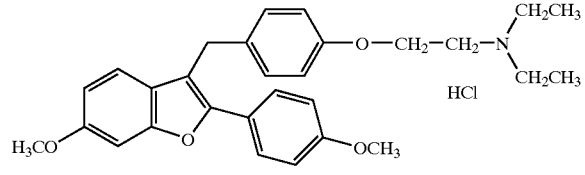

900 mg of the free base in Example 23 was converted to its hydrochloride salt in the manner described in Example 3. This yielded 370 mg of the title compound as an amorphous solid.

$^1$HNMR: Consistent with the proposed structure. MS: m/e=459 (M–HCl) FD; Analysis for the title compound: Theory: C, 70.22; H, 6.93; N, 2.82. Found: C, 69.97; H. 6.90; N, 2.75.

EXAMPLE 25

[2-(4-Methoxyphenyl)-6-methoxybenzofuran-3-yl]
[4-[2-diisopropylaminoethoxy]phenyl]methanol

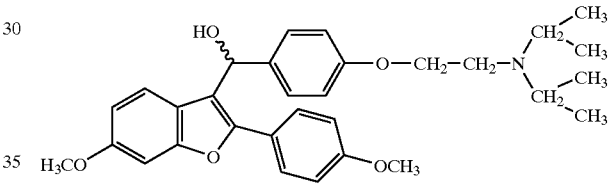

1.5 g (3 mmol) of [2-(4-methoxyphenyl)-6-methoxybenzofuran-3-yl][4-[2-diisopropylaminoethoxy]phenyl]methanone was reduced to the carbinol by the method described in Example 1. This yielded 830 mg of the title compound as an oily solid.

$^1$HNMR: Consistent with the proposed structure. MS: m/e=503 (M) FD; Analysis for the title compound: Theory: C, 73.93; H, 7.40; N, 2.78. Found: C, 73.64; H, 7.21; N, 2.49.

EXAMPLE 26

[2-(4-Methoxyphenyl)-6-methoxybenzofuran-3-yl]
[4-[2-diisopropylaminoethoxy]phenyl]methane

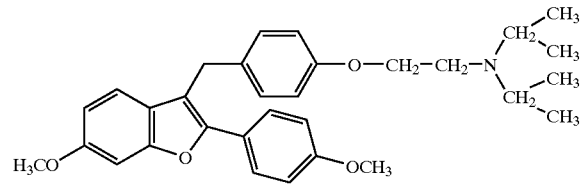

800 mg (1.6 mmol) of the carbinol from Example 25 was reduced by the method of Example 2. This yielded 630 mg of the title compound as an oil.

$^1$HNMR: Consistent with the proposed structure. MS: m/e=488 (M+1) FD; $C_{31}H_{37}NO_4$.

EXAMPLE 27

[2-(4-Methoxyphenyl)-6-methoxybenzofuran-3-yl][4-[2-diisopropylaminoethoxy]phenyl]methane Hydrochloride

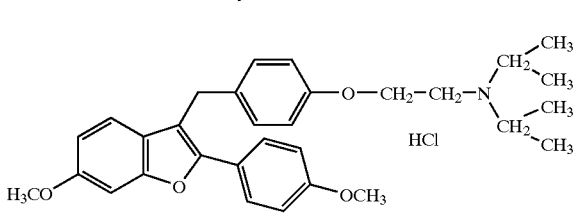

700 mg of the free base in Example 26 was converted to its hydrochloride salt by the method described in Example 3. The product was cystallized from ethyl acetate-ethanol, which yielded 110 mg of the title compound.

¹HNMR: Consistent with the proposed structure. MS: m/e=487 (M–HCl) FD; Analysis for the title compound: Theory: C, 71.04; H, 7.31; N, 2.68. Found: C, 70.84; H, 7.35; N, 2.63.

EXAMPLE 28

[2-Phenyl-6-methoxybenzofuran-3-yl][4-[2-(1-piperidinyl) ethoxy]phenyl]methanol

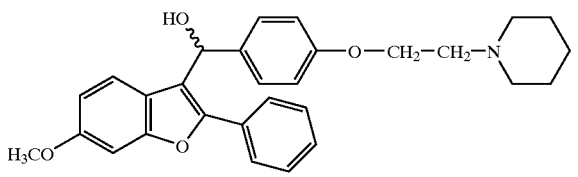

1.47 g (3 mmol) of [2-phenyl-6-methoxybenzofuran-3-yl][4-[2-(1-piperidinyl) ethoxy]phenyl]methanone hydrochloride was reduced by the method described in Example 1. This yielded 1.08 g of the title compound as an oil.

¹HNMR: Consistent with the proposed structure. MS: m/e=457 (M) FD; $C_{29}H_{31}NO_4$.

EXAMPLE 29

[2-Phenyl-6-methoxybenzofuran-3-yl][4-[2-(1-piperidinyl)ethoxy]phenyl]methane

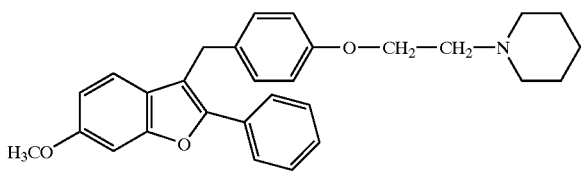

1.08 g (2.4 mmol) of the carbinol from Example 28 was reduced by the method described in Example 2. This yielded 940 mg of the title compound as an oil.

¹HNMR: Consistent with the proposed structure. MS: m/e=441 (M) FD; $C_{31}H_{31}NO_3$.

EXAMPLE 30

[2-Phenyl-6-methoxybenzofuran-3-yl][4-[2-(1-piperidinyl)ethoxy]phenyl]methane Hydrochloride

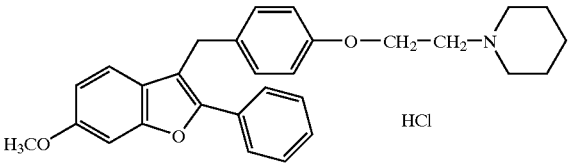

1.0 g of the free base in Example 29 was converted to its hydrochloride salt by the method of Example 3. The product crystallized from the ether-hydrochloric acid solution and was filtered and washed with ether, then dried. This yielded 630 mg of the title compound.

¹HNMR: Consistent with the proposed structure. MS: m/e=441 (M–HCl) FD; Analysis for the title compound: Theory: C, 72.86; H, 6.75; N, 2.93. Found: C, 72.74; H, 6.78; N, 2.94.

EXAMPLE 31

[2-(4-Methoxyphenyl)benzofuran-3-yl][4-[2-(1-piperidinyl)ethoxy]phenyl]methanol

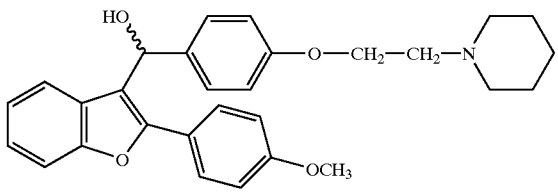

1.47 g (3 mmol) of [2-(4-methoxyphenyl)benzofuran-3-yl][4-[2-(1-piperidinyl)ethoxy]phenyl]methanone hydrochloride was reduced by the method described in Example 1. This yielded 880 mg of the title compound as an oil.

¹HNMR: Consistent with the proposed structure. MS: m/e=457 (M) FD; $C_{29}H_{31}NO_4$.

EXAMPLE 32

[2-(4-Methoxyphenyl)benzofuran-3-yl][4-[2-(1-piperidinyl)ethoxy]phenyl]methane

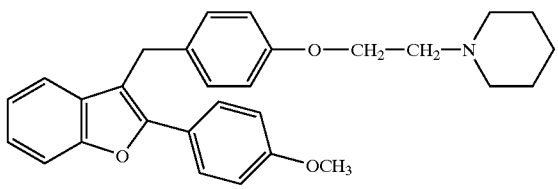

880 mg (1.75 mmol) of the carbinol from Example 31 was reduced by the method described in Example 2. This yielded 650 mg of the title compound as an oil.

¹HNMR: Consistent with the proposed structure. MS: m/e=441 (M) FD; $C_{29}H_{31}NO_3$.

EXAMPLE 33

[2-(4-Methoxyphenyl)benzofuran-3-yl][4-[2-(1-piperidinyl)ethoxy]phenyl]methane Hydrochloride

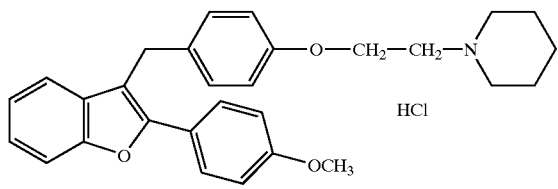

600 mg of the free base in Example 32 was converted to its hydrochloride salt in the manner described in Example 3. The compound crystallized from the ether-hydrochloric acid solution. The compound was filtered, washed with ether, and dried. This yielded 380 mg of the title compound.

$^1$HNMR: Consistent with the proposed structure. Analysis for the title compound: Theory: C, 72.86; H, 6.75; N, 2.93. Found: C, 72.66; H, 6.88; N, 3.11.

EXAMPLE 34

[2-(4-Methoxyphenyl)-6-methoxybenzofuran-3-yl][4-[2-(1-hexamethyleneimine)ethoxy]phenyl]methanol

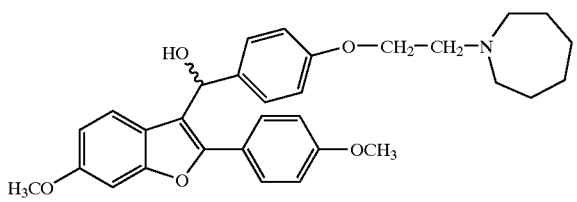

1.5 g (3 mmol) of [2-(4-methoxyphenyl)-6-methoxybenzofuran-3-yl][4-[2-(1-hexamethyleneimine)ethoxy]phenyl]methanone was reduced to the carbinol by the method described in Example 1. This yielded 1.15 g of the title compound as an oil.

$^1$HNMR: Consistent with the proposed structure. MS: m/e=501 (M) FD; $C_{31}H_{35}NO_5$.

EXAMPLE 35

[2-(4-Methoxyphenyl)-6-methoxybenzofuran-3-yl][4-[2-(1-hexamethyleneimine)ethoxy]phenyl]methane

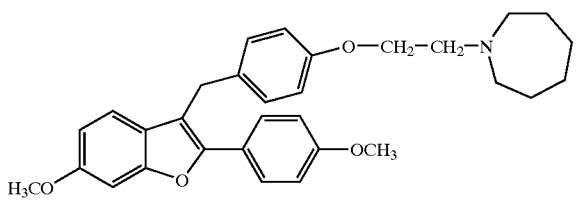

1.15 g (2.3 mmol) of the carbinol from Example 34 was reduced by the method described in Example 2. This yielded 900 mg of the title compound as an oil.

$^1$HNMR: Consistent with the proposed structure. MS: m/e=485 (M) FD; $C_{31}H_{35}NO_4$.

EXAMPLE 36

[2-(4-Methoxyphenyl)-6-methoxybenzofuran-3-yl][4-[2-(1-hexamethyleneimine)ethoxy]phenyl]methane Hydrochloride

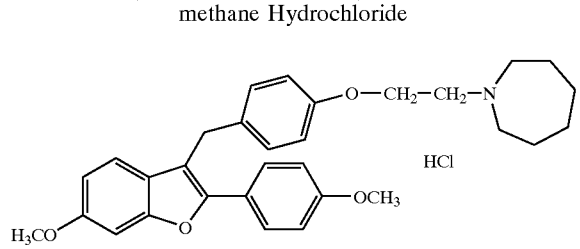

1.05 g of the free base Example 35 was converted to its hydrochloride salt by the method described in Example 3. The product was recrystallized from ethyl acetate-ethanol. This yielded 170 mg of the title compound.

$^1$HNMR: Consistent with the proposed structure.

The compounds of formula I of the present invention are useful for alleviating the symptoms of post-menopausal syndrome, particularly osteoporosis, associated cardiovascular diseases, particularly estrogen-dependent breast and uterine carcinoma. The term "alleviating" is defined to include prophylactically treating a woman from incurring one or more symptoms/pathological conditions of post-menopausal syndrome, holding in check such symptoms/pathological conditions, and/or treating existing symptoms/pathological conditions. As such, the present methods include both medical therapeutic and/or prophylactic treatment, as appropriate.

Compounds of formula I, also are effective for inhibiting uterine fibroid disease and endometriosis in women, and smooth muscle cell proliferation in humans. The following non-limiting test examples illustrate the methods of the present invention.

TEST PROCEDURE

General Preparation Procedure

In the examples illustrating the methods, a post-menopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection.

After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis.

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay.

Uteri were kept at 4° C. until time of enzymatic analysis. The uteri were then homogenized in 50 volumes of 50 mM Tris buffer (pH −8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound.

17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the present invention. Although $EE_2$ caused a decrease in serum cholesterol when orally administered at 0.1 mg/Kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the present invention generally reduce serum cholesterol compared to the ovariectomized control animals, but uterine weight was only minimally increased to slightly decreased. Compared to estrogenic compounds known in the art, the benefit of serum cholesterol reduction without adversely affecting uterine weight is quite rare and desirable.

As is expressed in the below data, estrogenicity also was assessed by evaluating the adverse response of eosinophil infiltration into the uterus. The compounds of the present invention did not cause any increase in the number of eosinophils observed in the stromal layer of ovariectomized rats, while estradiol caused a substantial, expected increase in eosinophil infiltration.

The data presented in the following Tables 1 and 2 reflect the response of 5 to 6 rats per treatment.

TABLE 1

| Compound | Dose mg/kg | Uterine Weight (% increase vs. OVX) | Uterine EPO (V. max) | Serum Cholesterol (% decrease vs. OVX) |
|---|---|---|---|---|
| $EE_2$* | 0.1 | 172.8 | 201.9 | 92.6 |
| Ex-3* | 0.1 | 8.6 | 4.7 | 38.9 |
|  | 1.0 | 26.3 | 5.8 | 53.0 |
|  | 10.0 | 30.1 | 11.3 | 73.3 |

*refers to the compound described in the stated Example, infra.

In addition to the demonstrated benefits of the compounds of the present invention, especially when compared to estradiol, the above data clearly demonstrate that compounds of Formula I are not estrogen mimetics. Furthermore, no deleterious toxicological effects (survival) were observed with any treatment.

Osteoporosis Test Procedure

Following the General Preparation Procedure, infra, the rats are treated daily for 35 days (6 rats per treatment group) and sacrificed by decapitation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and scanned at the distal metaphysis 1 mm from the patellar groove with single photon absorptiometry. Results of the densitometer measurements represent a calculation of bone density as a function of the bone mineral content and bone width, and demonstrate the activity of tested compounds.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) maintenance medium). Ten days prior to assay, MCF-7 cells are switched to maintenance medium supplemented with 10% dextran-coated charcoal stripped fetal bovine serum (DCC-FBS) assay medium in place of 10% FBS to deplete internal stores of steroids. MCF-7 cells are removed from maintenance flasks using cell dissociation medium (Ca++/Mg++ free HBSS (phenol red-free) supplementad with 10 mM HEPES and 2 mM EDTA). Cells are washed twice with assay medium and adjusted to 80,000 cells/mL. Approximately 100 µL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 µL transferred to triplicate microcultures followed by 50 µL assay medium for a final volume of 200 µL. After an additional 48 hours at 37° C. in a 5% $CO_2$ humidified incubator, microcultures are pulsed with tritiated thymidine (1 uCi/well), for 4 hours. Cultures are terminated by freezing at −70° C. for 24 hours followed by thawing and harvesting of microcultures using a Skatron Semiautomatic Cell Harvester. Samples are counted by liquid scintillation using, for example, a Wallac BetaPlace β counter.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of Fibroid Tumors in Guinea Pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of Human Uterine Fibroid Tissue in Nude Mice.

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri are harvested to assess the status of the organ.

Test 5

A. Tissue from Human Uterine Fibroid Tumors is Harvested and Maintained, In Vitro, as Primary Nontransformed Cultures.

Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical Induction of Endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of Human Endometrial Tissue in Nude Mice.

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri are harvested to assess the status of the intact endometrium.

Test 4

A. Tissue from Human Endometrial Lesions is Harvested and Maintained In Vitro as Primary Nontransformed Cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of restenosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethenyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation. The following formulation examples only are illustrative and are not intended to limit the scope of the present invention.

FORMULATIONS

In the formulations which follow, "active ingredient" means a compound of formula I, or a salt thereof.

Formulation 1

Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2

Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3

Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4

Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5

Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6

Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An Intravenous Formulation is Prepared as Follows:

Formulation 7

Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8

Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9

Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10

Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:

1. A compound of the formula:

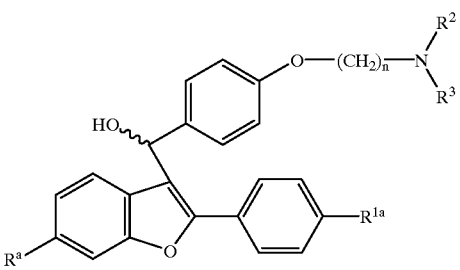

wherein
 $R^a$ is —OH or
  —O—($C_1$-$C_4$ alkyl);
 $R^{1a}$ is —OH or
  —O—($C_1$-$C_4$ alkyl);
 n is 2 or 3;
 $R^2$ and $R^3$ are each independently:
  —$C_1$-$C_4$ alkyl, or
  combine to form
   1-piperidinyl,
   1-pyrrolidinyl,
   1-pyrrolidinyl substituted with one or two methyl groups,
   4-morpholino or
   1-hexamethyleneimino;
 or a pharmaceutically acceptable salt thereof.

2. The compound of claim 1, wherein $R^a$ is —OH, $R^{1a}$ is —OH, $R^2$ and $R^3$ combine to form 1-piperidinyl and n=2.

3. The compound of claim 1, wherein $R^a$ is —O—$CH_3$, $R^{1a}$ is —O—$CH_3$, $R^2$ and $R^3$ combine to form 1-piperidinyl and n=2.

4. The compound of claim 1, wherein $R^a$ is —OH, $R^{1a}$ is —OH, $R^2$ and $R^3$ combine to form hexamethyleneimino and n=2.

5. The compound of claim 1, wherein $R^a$ is —OH, $R^{1a}$ is —OH, $R^2$ and $R^3$ combine to form 1-pyrrolidinyl and n=2.

6. The compound of claim 1, wherein $R^a$ is —O—$CH_3$, $R^{1a}$ is —O—$CH_3$, $R^2$ and $R^3$ are each independently —$CH_3$ and n=2.

7. The compound of claim 1, wherein $R^a$ is —O—$CH_3$, $R^{1a}$ is —O—$CH_3$, $R^2$ and $R^3$ are each independently —$CH_2$—$CH_3$ and n=2.

8. The compound of claim 1, wherein $R^a$ is —O—$CH_3$, $R^{1a}$ is —O—$CH_3$, $R^2$ and $R^3$ are each independently isopropyl (—CH—$(CH_3)_2$) and n=2.

9. The compound of claim 1, wherein $R^a$ is —O—$CH_3$, $R^{1a}$ is —O—$CH_3$, $R^2$ and $R^3$ combine to form hexamethyleneimino and n=2.

10. A compound according to claim 1 wherein $R^a$ and $R^{1a}$ each are —$OCH_3$.

11. A compound according to claim 10 wherein $R^2$ and $R^3$ are combined to form 1-piperidinyl.

12. A compound according to claim 11 wherein said salt thereof is the hydrochloride salt.

13. A compound according to claim 1 wherein $R^a$ and $R^{1a}$ each are —OH.

14. A compound according to claim 13 wherein $R^2$ and $R^3$ are combined to form 1-piperidinyl.

15. A compound according to claim 14 wherein said salt thereof is the hydrochloride salt.

* * * * *